(12) United States Patent
Franklin

(10) Patent No.: US 9,186,464 B2
(45) Date of Patent: Nov. 17, 2015

(54) DOSING INJECTOR

(71) Applicant: Allergan, Inc., Irvine, CA (US)

(72) Inventor: Ethan Franklin, Goleta, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/828,159

(22) Filed: Mar. 14, 2013

(65) Prior Publication Data

US 2013/0197449 A1 Aug. 1, 2013

Related U.S. Application Data

(63) Continuation-in-part of application No. 12/121,000, filed on May 15, 2008.

(60) Provisional application No. 61/758,698, filed on Jan. 30, 2013.

(51) Int. Cl.
*A61M 5/00* (2006.01)
*A61M 5/315* (2006.01)
*A61M 5/31* (2006.01)

(52) U.S. Cl.
CPC ......... *A61M 5/31526* (2013.01); *A61M 5/3158* (2013.01); *A61M 5/31581* (2013.01); *A61M 5/31595* (2013.01); *A61M 5/3129* (2013.01); *A61M 5/3157* (2013.01); *A61M 5/31511* (2013.01); *A61M 2005/31506* (2013.01); *A61M 2005/31508* (2013.01)

(58) Field of Classification Search
CPC ............... A61M 2005/202; A61M 2005/2073; A61M 5/31526; A61M 5/31528; A61M 5/31595; A61M 5/31581
USPC ......... 604/110, 218, 208, 209, 210, 207, 224, 604/228; 600/432
See application file for complete search history.

(56) References Cited

U.S. PATENT DOCUMENTS

| 3,161,323 | A | * | 12/1964 | Bent ................................ 222/41 |
| 4,950,163 | A | * | 8/1990 | Zimble ........................ 433/215 |
| 6,595,979 | B1 | | 7/2003 | Epstein et al. |
| 7,611,495 | B1 | * | 11/2009 | Gianturco ..................... 604/207 |
| 2003/0004467 | A1 | | 1/2003 | Musick et al. |

FOREIGN PATENT DOCUMENTS

| WO | WO2005/102420 A1 | 11/2005 |
| WO | WO2008/032216 A1 | 3/2008 |
| WO | WO2012/085208 A1 | 6/2012 |

* cited by examiner

*Primary Examiner* — Kevin C Sirmons
*Assistant Examiner* — Brandy S Lee
(74) *Attorney, Agent, or Firm* — Brigitte C. Phan; Ted A. Chan; Debra D. Condino

(57) ABSTRACT

A metered dose syringe includes a barrel having an open end and a opposing spaced apart port adapted to receive a needle. A plunger rod is provided and slidably disposed within the barrel through the barrel open end. Structure interconnected with the barrel and the plunger rod is provided for enabling stepwise movement of the plunger rod within the barrel. A syringe within the scope of our present invention permits injection of repeated and accurate doses due to the physical stops or dosage administered indicators.

1 Claim, 10 Drawing Sheets

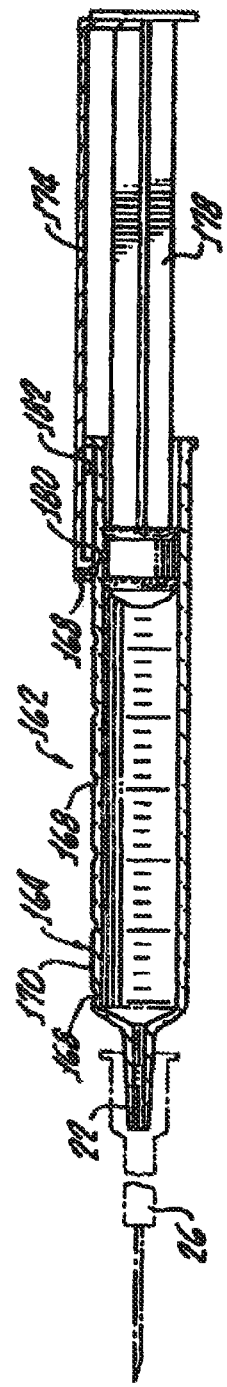
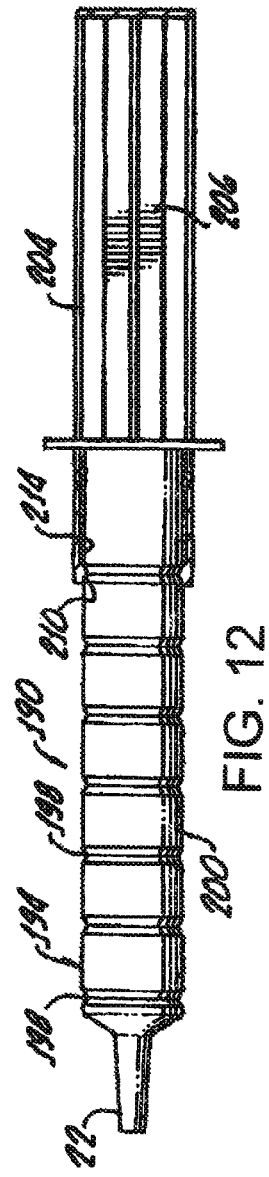
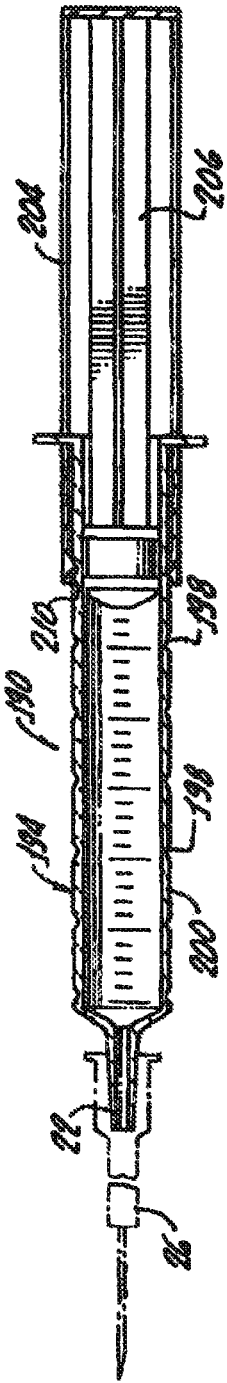
FIG. 11
FIG. 12
FIG. 13

DOSING INJECTOR

CROSS-REFERENCE TO RELATED APPLICATIONS

This application is a continuation-in-part of U.S. patent application Ser. No. 12/121,000, filed May 15, 2008 and claims the benefit of priority pursuant to 35 U.S.C. §119(e) to U.S. provisional patent application Ser. No. 61/758,698, filed Jan. 30, 2013, incorporated herein in its entireties by reference.

FIELD

The present invention relates to devices such as a syringe or syringe-like device that allow for repeated and accurate dosing of substances such as a neurotoxin.

BACKGROUND

There are many types of syringes available for medical (injections, instillations, etc.) and non-medical (basting/cooking, adhesive, lubrications, other industrial/manufacturing) uses. Over the years, there have been many enhancements to the basic syringe. These include, but are not limited to syringes that are disposable, include luer locks, have safety mechanisms to minimize needle sticks, are dedicated to medication cartridge systems (such as Carpujects®), as well as syringes that are factory pre-filled with a unit dose/aliquot of medication or other fluid.

With most syringes, by applying pressure to the piston, and controlling where the piston stops relative to tick marks indicating volumes delivered, the operator can administer multiple aliquots (equal or unequal) of fluid from the same syringe in order to deliver a predetermined total amount of fluid to a target location.

However, this takes good hand-to-eye coordination. In certain applications, such as delivery of multiple doses of medication sequentially during the same patient visit, it can be important to deliver very accurate amounts of fluid in a quick, convenient, precise and accurate manner.

There is a need for a syringe or a syringe-like device that can provide for repeated and accurate dosing of a substance, and allow the operator to concentrate on other important aspects of the associated procedures.

SUMMARY

A metered, multiple aliquot/dose syringe in accordance with the present invention generally includes a barrel having an open end and a opposing spaced apart port adapted to receive a needle. A piston is provided and slidably disposed within the barrel through the barrel open end and a push rod is connected to the piston for sliding the piston within the barrel.

In accordance with the present invention, structure is provided which interconnects the barrel and the push rod for enabling stepwise movement of the push rod and the piston within the barrel. This structure further provides concomitant tactile and/or an audible (sound) indication of such stepwise movement, thereby enabling the user to operate the syringe in delivering multiple doses without the visual observance thereof.

Thus, a syringe within the scope of our present invention permits injection of accurate doses due to the physical stops or dosage administered indicators (i.e. elements 58 in FIG. 1, 22 in FIG. 6, 138 in FIG. 8, and elements 68 in FIG. 10) which can act to prevent hydraulic momentum from continuing to deliver fluid after thumb pressure is lifted off the push rod (piston).

More particularly, the structure in accordance with one embodiment of the present invention may include the plurality of spaced apart ridges on an outer surface of the push rod and an engageable ridge disposed on an inner surface of the barrel.

In another embodiment of the present invention, the structure comprises a plurality of spaced apart detents in an outer surface of the push rod and a corresponding engageable ridge disposed on an inner surface of the barrel.

Still another embodiment of the present invention, the structure comprises a plurality of spaced apart ridges disposed on an outer surface of the barrel and an arm connected to the push rod. The arm includes a ridge disposed for stepwise engagement of the spaced apart ridges. More particularly, the spaced apart ridges may be aligned with one another only a portion of the barrel circumference and the arm may have a width smaller than a push rod circumference.

Yet another embodiment of the present invention, the structure includes a plurality of spaced apart ridges disposed on an outer surface of the barrel and a sleeve is provided which surrounds the push rod and includes a ridge disposed on an inner surface of the sleeve for stepwise engagement of the spaced apart ridges. More specifically, in this embodiment, the spaced apart ridges are circumferential about the barrel and the sleeve ridge is circumferential about the sleeve inner surface.

A further embodiment in accordance with the present invention includes structure which comprises a plurality of spaced apart detents disposed on an outer surface of the barrel and an arm connected to the push rod with the arm including a ridge disposed for a stepwise engagement of the spaced apart detents. More particularly, in this embodiment, the spaced apart detents may be aligned with one another over a portion of the barrel structure and the arm has a width smaller than a push rod circumference.

An additional embodiment of the present invention provides for a syringe in which the structure comprises a plurality of spaced apart detents disposed on an outer surface of the barrel and a sleeve surrounding the push rod includes a ridge disposed on an inner surface of the sleeve for stepwise engagement of the spaced apart detents. More particularly, in this embodiment, the spaced apart detents may be circumferential about the barrel and the sleeve ridge may be circumferential about the sleeve inner surface.

In another aspect, the present invention provides a dosing injector that includes a dosing mechanism that allows for repeated and accurate dosing of a substance such as a neurotoxin.

In certain embodiments, a dosing injector is provided that includes a dosing mechanism that allows for repeated and accurate dosing of a substance, and an override mechanism that allows a user to disengage from the dosing mechanism.

DRAWINGS

The advantages and features of the present invention will be better understood by the following description when considered in conjunction with the accompanying drawings, in which:

FIG. 1 illustrates a metered, multiple aliquot-dose syringe in accordance with the present invention which generally includes a barrel, a piston slidably disposed therein along with a push rod connected to the piston and a structure interconnected to the barrel and the piston for enabling stepwise movement of the push rod and the piston within the barrel, more specifically, the structure may include a plurality of spaced apart ridges on an outer surface of the piston and an engageable ridge disposed on an inner surface of the barrel;

FIG. 2 is an illustration of the use of the present invention with a cystoscope for visualizing and performing procedures in a bladder while at the same time utilizing tactile and sound features of the present invention;

FIGS. 3, 4, and 5 illustrate alternative ridge and detent configurations encompassed by the present invention;

FIG. 11 is a cross sectional view of the embodiment shown in FIG. 10;

FIG. 12 is a plan view of still another embodiment of the present invention utilizing a barrel having a plurality of spaced apart circumferential detent in a barrel and a corresponding ridge formed in a sleeve surrounding a push rod;

FIG. 13 is a cross sectional view of the embodiment shown in FIG. 12;

FIGS. 14 to 17B illustrate a dosing device in accordance with another aspect of the present invention; wherein:

FIG. 14 is an isometric view of a dosing device in accordance with an embodiment of the present invention; the device includes a syringe, a plunger rod slidably disposed therein and and a control component interconnecting the syringe and the plunger rod;

FIG. 15 is a cross sectional view of the device shown in FIG. 14;

FIGS. 17A and 17B show a control component of an alternative dosing device in accordance with aspects of the present invention.

DESCRIPTION

Figure 1:
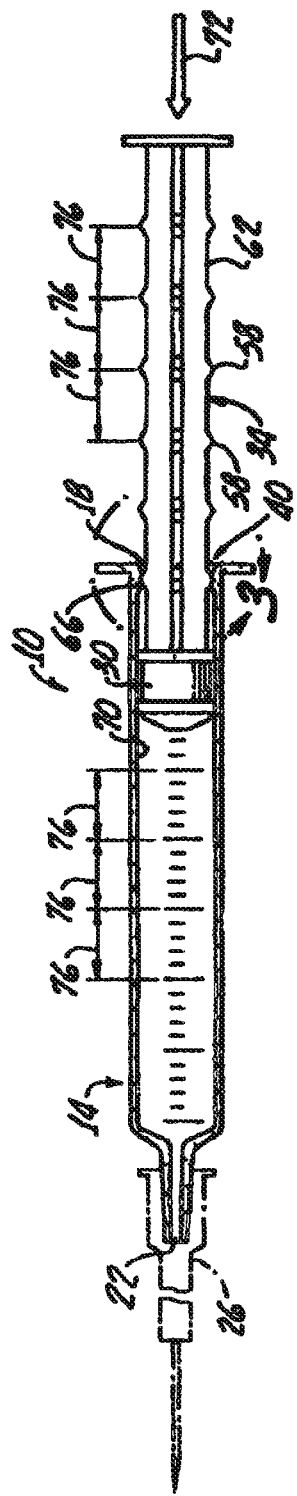

With reference to FIG. 1, there is shown a syringe 10 in accordance with the present invention for providing a metered multiple aliquot/dose that includes a barrel 14 having an open end 18 and an opposing spaced apart port 22 which is adapted for receiving a conventional needle 26, shown in broken line. A piston 30 is slidably disposed within the barrel 14 through the barrel open end 18 and a push rod 34 is connected to the piston for sliding the piston 30 within the barrel 14.

Structure 40 interconnecting the barrel 14 and the push rod 34 enables stepwise movement of the push rod 34 and the piston 30 within the barrel 14.

Figure 2:
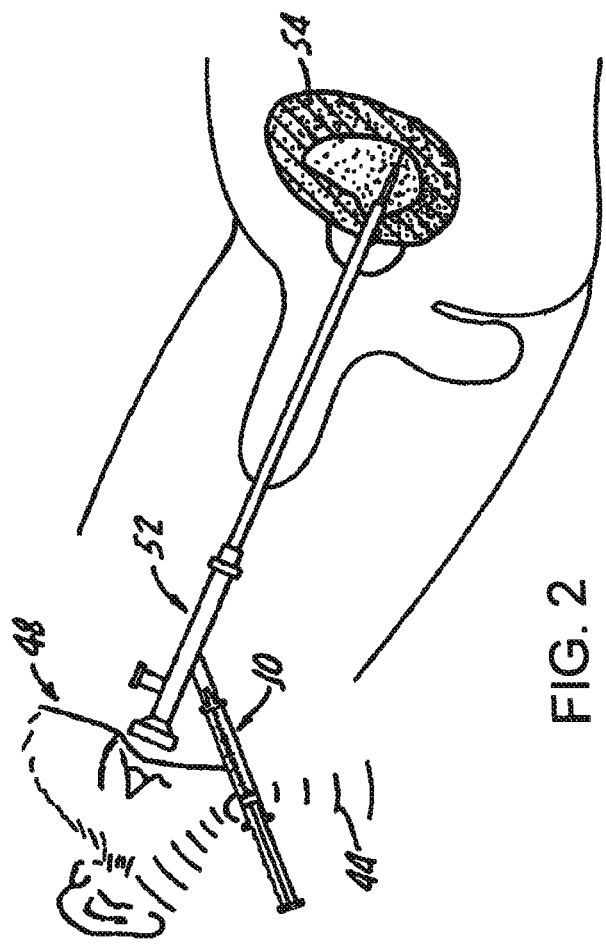

As will be described hereinafter in greater detail, the structure 40 is configured for producing sound indication as indicated by lines 44, in FIG. 2 of stepwise movement of the push rod 34 and piston 30 within the barrel 14 to enable an operator 48 to deliver multiple doses of a medicament without visual observation of the syringe 10. This is particularly useful in the delivery of a drug using an endoscope 52 as shown in FIG. 2.

As the operator 48 (such as a surgeon or urologist) is busy manipulating the scope 52 so that he/she can visualize the proper area of the body tissue 54, in the absence of an assistant, he/she also needs to control the syringe 10, place and secure the scope 52, and then let go of the scope 52 with one hand to grasp then push the syringe 10.

During this time, the scope 52 and needle 10 have a tendency to move. In prior art discoveries, the hydraulic momentum of the initial piston (not shown) push, may cause the piston to move past a desired point on a barrel (not shown), leading to too much fluid being administered at each injection site. The syringe 10 in accordance with the present invention prevents this over-run by having "ratcheted stops" spaced at proper distance for the desired volume to be delivered. It will further enable the procedure to be conducted by one person without the need for an assistant as the endoscopic operator 48 will not have to take his eyes off the image being relayed through the scope 52.

Figure 3:
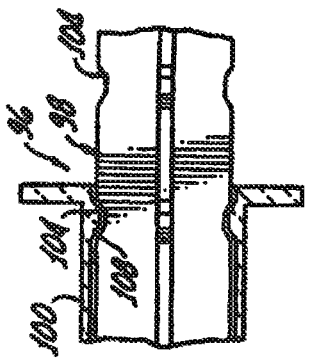

With reference again to FIG. 1, in accordance with the present invention, the structure 40 includes a plurality of spaced apart ridges 58 disposed on an outer surface 62 of the push rod 34 and an engageable ridge 66 disposed on an inner surface 70 of the barrel 14. Movement of the push rod 34 in a direction indicated by arrow 72 causes stepwise engagement between the ridges 58, 66 resulting not only in a tactile sensation by the operator 48 but also in sound generation as indicated at lines 44 in FIG. 2. Selected spacing 76 may provide for one milliliter doses, as an example, to be ejected from a multi-milliliter syringe. Thus, the syringe 10 in accordance with the present invention provides for an accurate and precise dose/aliquot of fluid administered in a fast and stepwise convenient manner. An enlargement of the structure 40 showing a ridges 58, 66 during engagement is illustrated in FIG. 3.

Figure 4:
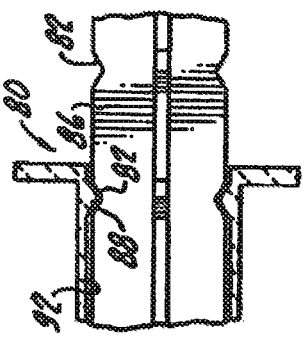

FIG. 4 is an alternative embodiment of the structure 80 in accordance with the present invention, wherein structure 80 comprises a plurality of detents 82 in a push rod outer surface 86 and a correspondingly engageable ridge 88 disposed on a barrel inner surface 92.

Figure 5:
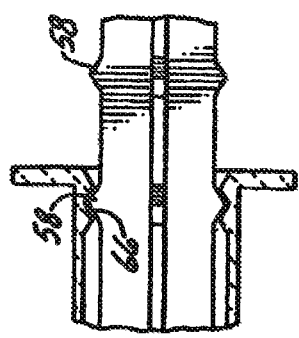

Control of the tactile sensory indication of stepwise movement provided by a structure 96 for a push rod 98 and barrel 100 is shown in FIG. 5 wherein a detents 104 and ridge 108 have a smoother contour than a corresponding ridges 82, 88 shown in FIG. 4 thereby changing a tactile and auditory sensing of movement of the push rod 98 within the barrel 100.

Figure 6:
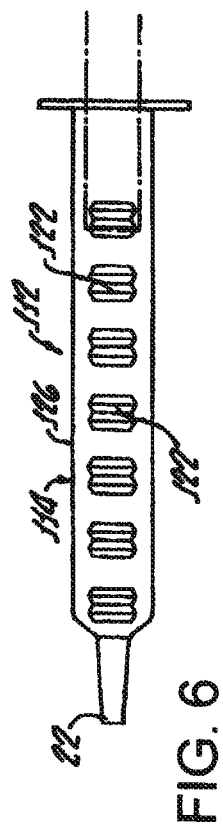
FIG. 6 is a plan view of an alternative embodiment of the present invention showing a barrel having a plurality of spaced apart ridges aligned with one another over a portion of the barrel.
Figure 7:
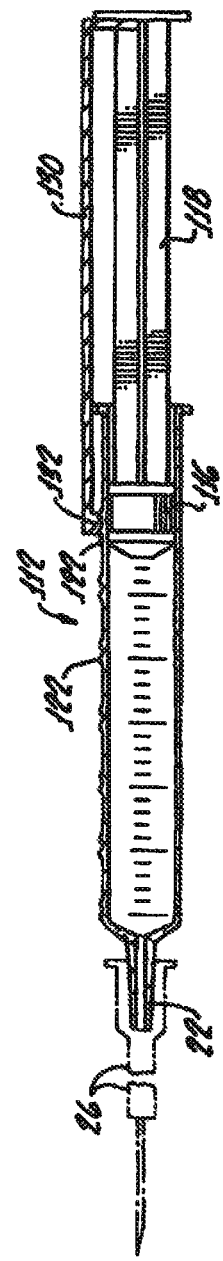
FIG. 7 is a cross sectional view of the barrel illustrated in FIG. 6 further showing an arm connected to the push rod with the arm including a ridge disposed for a stepwise engagement of the spaced apart ridges on the barrel.

In yet another embodiment syringe 112 is illustrated in FIGS. 6 and 7 which includes a barrel 114, piston 116, and a push rod 118. The syringe barrel 114, as illustrated in FIGS. 6 and 7, includes a plurality of spaced apart ridges 122 disposed on an outer surface 126 of the barrel 114 and an arm 130 connected to a push rod 118 which includes an arm ridge 132 for a stepwise engagement with the ridges 122. In this syringe 112, the ridges 122 are aligned with one another over a portion of the barrel 114 circumference, or outer surface, 126 and the arm 130 has a width smaller than a circumference of the push rod 118.

Figure 8:
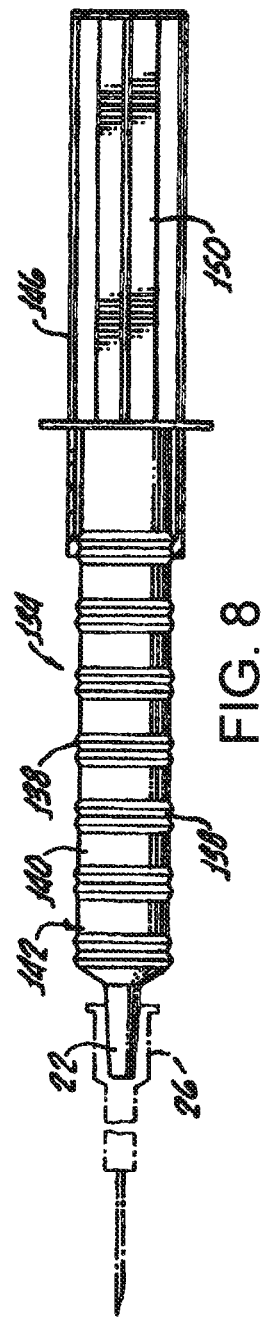
FIG. 8 is a plan view of an alternative embodiment of the present invention in which the barrel includes circumferential ridges and a sleeve connected to the push rod includes a ridge disposed on an inner surface of the sleeve for a stepwise engagement of the spaced apart ridges.
Figure 9:
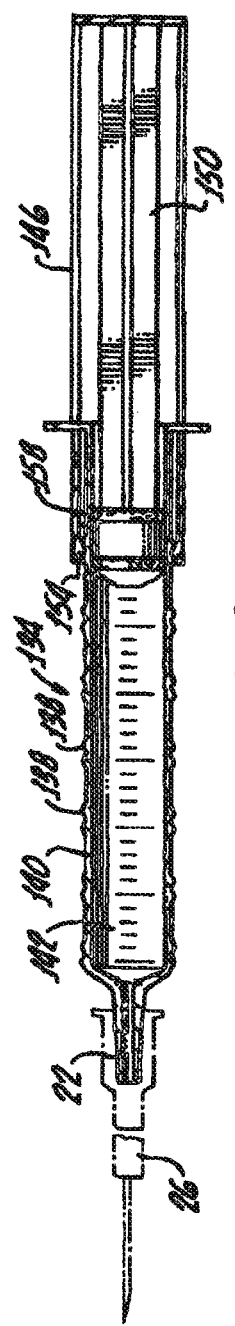
FIG. 9 is a cross sectional view of the embodiment shown in FIG. 8.

In yet another embodiment syringe 134 is illustrated in FIGS. 8 and 9 with common character references indicating identical or substantially similar elements as hereinbefore discussed in connection with other embodiments of the present invention.

As shown in FIGS. 8 and 9, the syringe 134 includes a plurality of spaced apart circumferential ridges 138 disposed on an outer surface 140 of a barrel 142, and a sleeve surrounds and is connected to a push rod 150. A circumferential ridge 154 disposed on an inner surface of the sleeve 146 enables stepwise engagement of the barrel ridges 138 in a manner as hereinabove described in connection with earlier described embodiments of the present invention.

Figure 10:
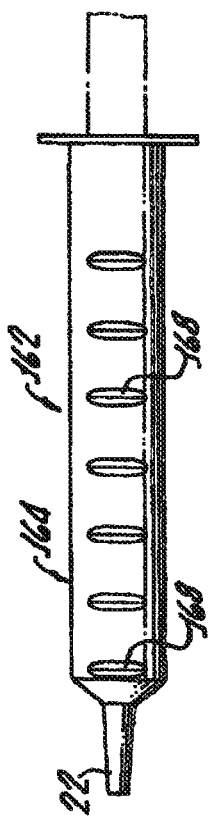
FIG. 10 is a plan view of yet another embodiment of the present invention illustrating a barrel having a plurality of spaced apart detents in an outer surface thereof along with a sleeve having a circumferential ridge for engaging the detents.

FIGS. 10 and 11 illustrate yet another embodiment syringe 162 in accordance with the present invention that includes a barrel 164 which includes a plurality of spaced apart detents 168 and an outer surface 170 of the barrel 164 and an arm 174 attached to a push rod 178 and includes a ridge 180 disposed on an arm inner surface 182 for a stepwise engagement with the detents 168 in a stepwise manner.

Still another embodiment syringe 190 is shown in FIGS. 12 and 13 which includes a barrel 194 having spaced apart circumferential detents 198 in a barrel outside surface 200 and a sleeve 204 surrounding a push rod 206 includes a ridge 210 disposed on an inside surface 214 of the sleeve 204 for stepwise engagement of the spaced apart detents 198.

A method in accordance with the present invention utilizes any one of the syringes 10, 112, 134, 162, 190 hereinabove described and includes with respect to syringe 10 disposing a medicament in the barrel 14 and operating the structure 40 interconnecting the barrel 114 and the push rod 34 to provide stepwise movement of the push rod 34 and piston 30 within the barrel 114 in order to administer metered multiple aliquot/doses of medicament.

In another aspect, the present invention provides a dosing device which provides, among other features, (1) a dosing mechanism allowing for repetitive, precise and accurate dosing of a substance; and (2) an override mechanism allowing for a user to disengage from the dosing mechanism.

Figure 14:
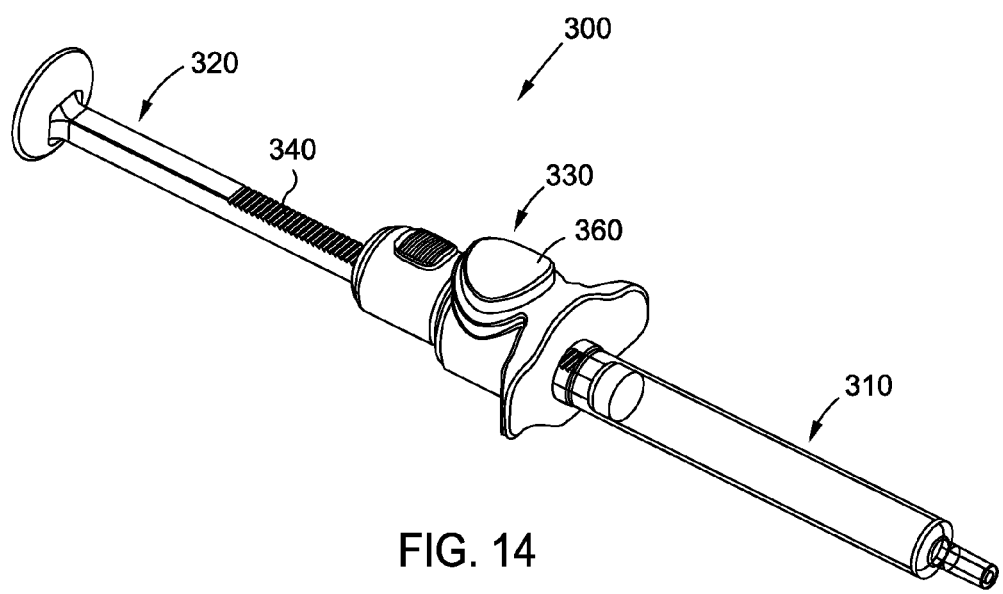

FIG. 14 is a perspective view of an exemplary embodiment of a dosing device 300 provided in accordance with aspects of the present invention. Briefly, the dosing device 300 comprises a syringe 310 connected to a plunger rod 320 by a control component 330. The syringe 310 can be a standard or custom syringe. It may or may not be prepackaged with the rest of the dosing device 300. The control component 330 comprises an actuator 360 for actuating the dosing device 300. In one embodiment, the actuator 360 is a button. In an alternative embodiment, the actuator 360 is a lever.

Figure 15:
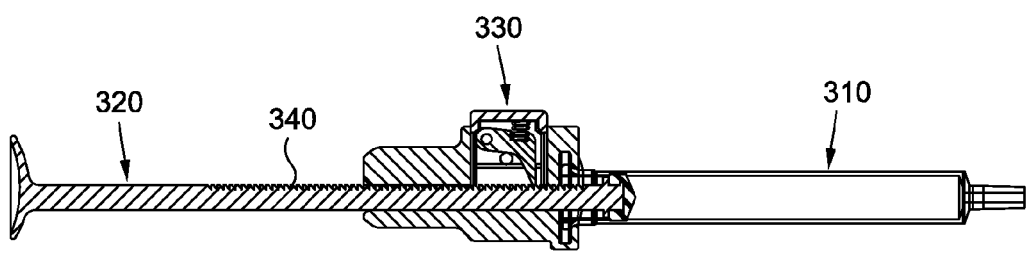
Figure 16A:
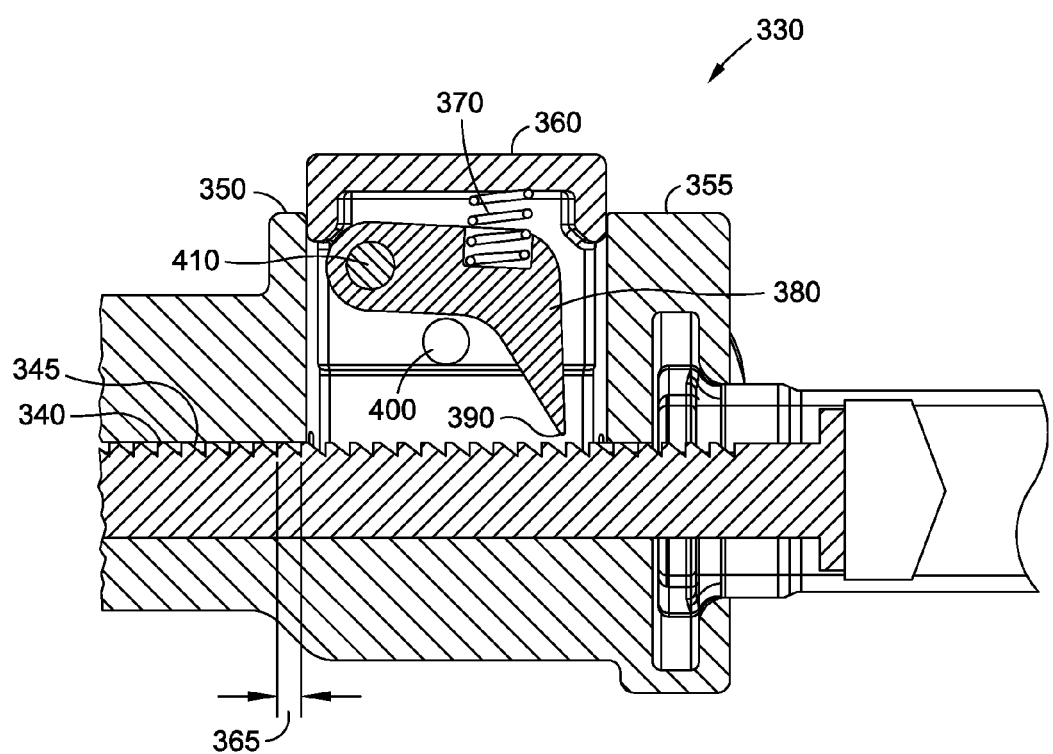
FIGS. 16A, 16B and 16c show cross-sectional views of the control component in three different positions according to aspects of the present invention.

As shown in FIG. 15, the plunger rod 320 comprises an engaging surface 340. In one embodiment, the engaging surface 340 comprises a rack having a plurality of spaced apart teeth 345. The spaced apart teeth 345 are uniformly spaced apart longitudinally over at least a portion of a surface of the push rod 320. The distance between one tooth to the next tooth defines an interdental space 365 or pitch, as shown in FIG. 16A. The interdental space 365 corresponds to a predetermined volume of liquid. In alternative embodiments, the engaging surface 340 comprises ridges, detents, or the like.

In one embodiment, the control component 330 is a plunger assembly. Plunger assemblies for use in dispensing devices have been described in for example U.S. Pat. No. 3,161,323, the content of which is incorporated herein in its entireties by reference.

Referring to FIGS. 15 and 16A, the control component 330 comprises a housing 350 having a top side 355, an actuator 360 for actuating the dosing device 300 to enable stepwise movement of the push rod 320 within the syringe 310 for repetitive and accurate delivery of a predetermined volume of a liquid composition disposed in the syringe. In one embodiment, the actuator 360 is a button. In an alternative embodiment, the actuator 360 is a lever. In one embodiment, the actuator 360 is movable vertically to various positions relative to the top side 355. In one embodiment, the actuator 360 has three basic positions, corresponding to different levels relative to the top side 355. In a fully extended position, the actuator 360 is at its maximum height. In a fully depressed position, the actuator 360 is at a minimum height relative to the top side 355. In a partly extended position, the actuator 360 is partly depressed and having a height intermediate between the maximum height and the minimum height. The motive force that lifts the actuator 360 back up can be provided by a spring or some other mechanical design element, as well known to one skilled in the art.

In one embodiment, the housing 350 houses a pawl 380 rotationally coupled to a pivot pin 410. In one embodiment, the pawl 380 has a wedge shaped end portion 390 which reversibly engages with the spaced apart teeth 345 on the engaging surface 340 in a dosing mechanism as described herein. A stopping pin 400 is positioned adjacent an inner side of the pawl 380 and limits clockwise movement of the pawl 380. A biasing element 370 connects the pawl 380 to the actuator 360. In one embodiment, the biasing element 370 is a spring.

Referring to FIG. 16A, in a reset or starting position, the actuator 360 is at its maximum height relative to the top side 355. The biasing element 370 is in an extended state. The end portion 390 of the pawl 380 is disengaged from the plurality of spaced apart teeth 345 on the engaging surface 340.

Figure 16B:
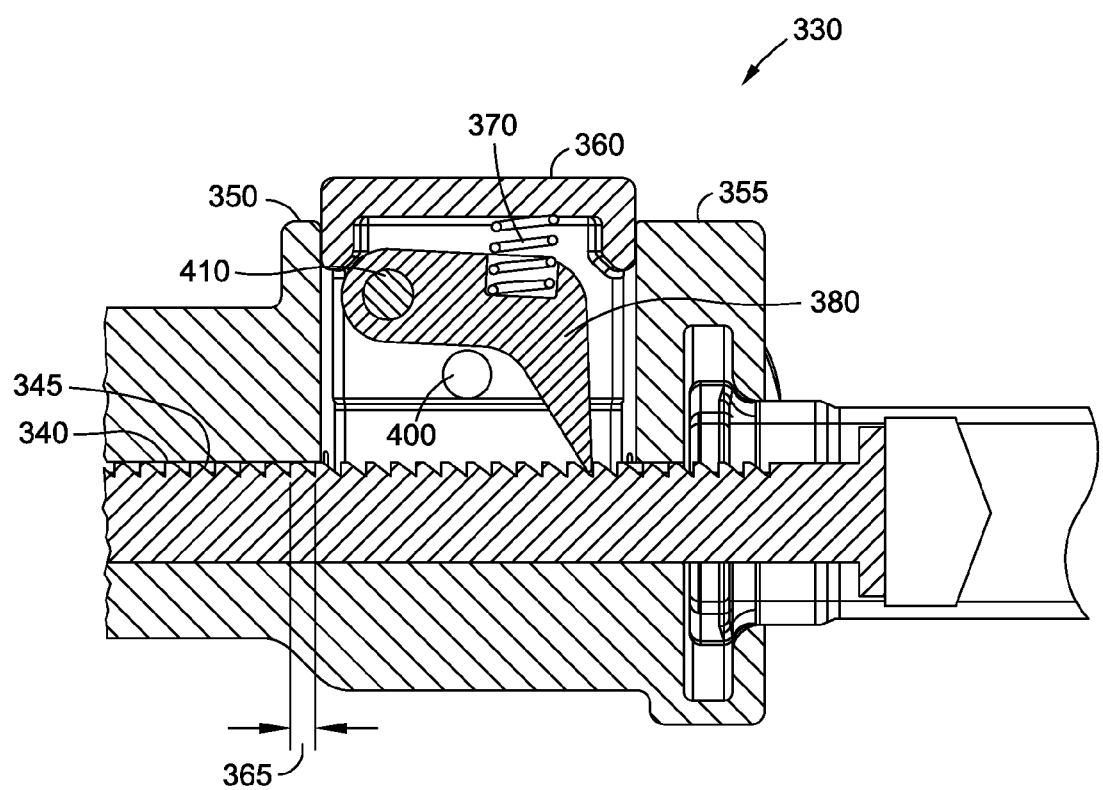

In a partly actuated position as shown FIG. 16B, the actuator 360 is partly depressed such that its height relative to the top side 355 is an intermediate height between the maximum height and the minimum height. Pressing the actuator 360 partly compresses the biasing element 370 which causes the end portion 390 to engage with an initial tooth 345 on the engaging surface 340. The biasing element 370 ensures that the end portion 390 of the pawl 380 remains engaged with the initial tooth 345.

Figure 16C:
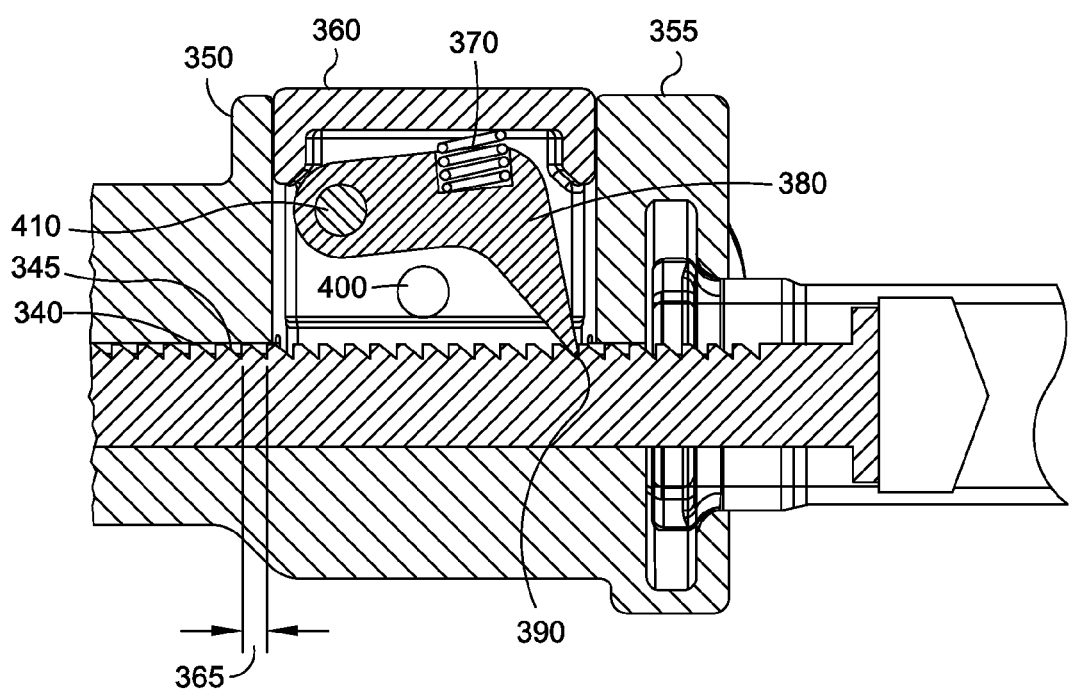

In a fully actuated position as shown in FIG. 16C, the actuator 360 is fully pressed down. The compression of the biasing element 370 causes the pawl 380 to tilt backward, pushing the plunger rod 320 and the engaging surface 340 forward. In this position, the pawl 380 is no longer in contact with the stopping pin 400. Once the actuator 360 is released from this position, the end portion 390 of the pawl 380 will disengage from the initial tooth 345 and align to engage the next tooth the next time the actuator is pressed. The interdental space between the spaced apart teeth 345 correlates with a desired dose. Each actuation of the actuator 360 causes the plunger rod 320 to advance exactly one increment corresponding to an interdental space 365 or pitch 365. In one embodiment, each actuation dispenses 0.1 ml. In alternative embodiments, each actuation dispenses a volume smaller than 0.1 ml. In yet other embodiments, each actuation dispenses a volume larger than 0.1 ml.

In one embodiment, the present dosing device provides an override mechanism, wherein a user has an option to freely pull the plunger rod 320 in either direction for aspiration, filling, evacuating, or dosing an amount other than an amount specified by the interdental space 365. To exercise the override mechanism, the user releases the actuator 360 such that it can return to its maximum height relative to the top side 355 as shown in FIG. 16A. In one embodiment, a pin (not shown) can be incorporated into the actuator 360 to maintain it in this position such that the pawl 380 is disengaged from the engaging surface 340 of the plunger rod 320. When ready, the user can remove the pin holding the actuator 360 in the fully extended position (for example, by using a pull tab accessible from the exterior of the device). Once the pin is removed, the biasing element 370 forces the pawl 380 to engage the engaging surface 340. This particular embodiment can prove useful when disengagement is only desired at the beginning of a procedure. For example, if an injection device is to be pre-filled with a diluent used for reconstitution, the user will want to inject that diluent freely, and then freely draw the reconstituted product back into the device. After the device is loaded, the user can then pull the tab and the device is setup to dose incrementally.

Thus, aspects of the present dosing device provides a dosing device, comprising: a barrel having an open end and an opposing spaced apart port adapted to receive a needle; a plunger rod slidably disposed within said barrel through the barrel open end; the plunger rod having a plurality of spaced apart teeth over at least a portion of a top side thereof and having interdental spaces therebetween; a control component interconnecting said barrel and said plunger rod. In one embodiment, the control component comprises a pawl having an end point configured for engaging with the plurality of spaced apart teeth; means for causing the end point to enter an interdental space, engage a tooth and move the plunger rod forwardly an increment corresponding to the interdental space to allow for stepwise movement of the plunger rod within the barrel; and an actuator for actuating the stepwise movement. In one embodiment, the actuator is movable from a reset position, wherein the end point is disengaged from the plurality of spaced apart teeth, to a partially actuated position, wherein the end point engages a first tooth, to a fully actuated position, wherein the end point moves from the first tooth to a second tooth; and wherein in the reset position, the plunger rod is freely slidable longitudinally the barrel.

Figure 17A:
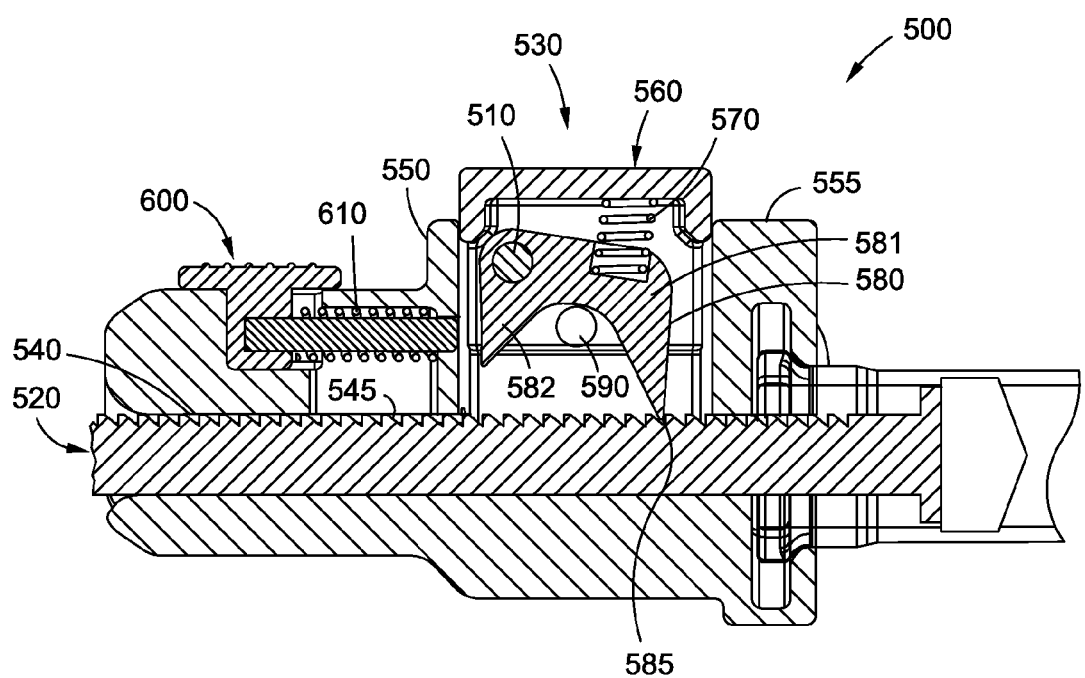
Figure 17B:
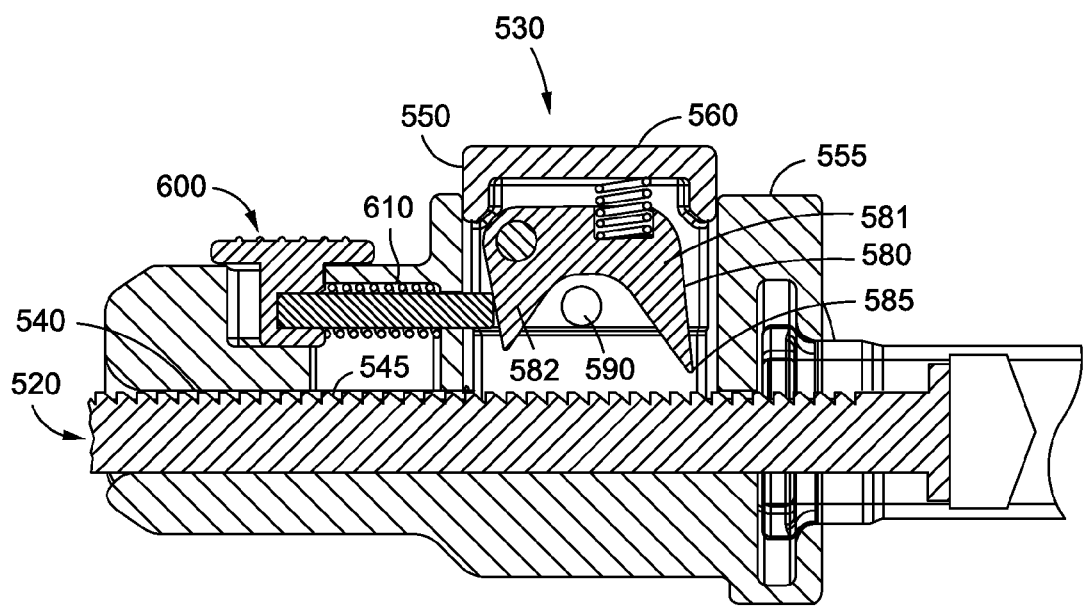

In an alternative embodiment shown in FIGS. 17A and 17B, a dosing device 500 comprises a control component 530. In one embodiment, the control component 530 comprises an actuator 560, a housing 550 having a top side 555 which houses a biasing element 570, a "double pawl" 580 rotationally coupled to a pivot pin 510 and a stopping pin 590 which limits clockwise movement of the pawl 580. The double pawl 580 has a first side 581 having an end point 585 engageable with the engaging surface 540 of the plunger rod 520 and a second side 582 which does not come into contact with the engaging surface 540. In one embodiment, the "double pawl" 580 is normally engaged with the plurality of spaced apart teeth 545 on the engaging surface 540 of the plunger rod 520. In one embodiment, the actuator 560 is movable from a resting position to an actuated position. In a resting state, the actuator 560 is positioned at a height relative to the top side 555 such that the biasing element 570 is partly compressed, keeping the end point 585 in engagement with one of the plurality of spaced apart teeth 545 on the engaging surface 540, as shown in FIG. 17A. In an actuated state, the actuator is depressed, causing the biasing element 570 to further compress. The compression of the biasing element 570 causes the pawl 580 to tilt backward, pushing the plunger rod 520 and the engaging surface 540 forward (not shown), in a similar mechanism as described for FIGS. 16A, B and C.

In one embodiment, the plunger assembly 530 is connected to a spring loaded slider actuator 600. As shown in FIG. 17A, in a locked position, a spring 610 connecting the slider actuator 600 to the housing 550 is in an extended state, and the slider actuator 600 is spaced apart from the second side 582 of the "double pawl" 580. In this locked position, a user cannot pull the plunger rod 520 back but he/she can control aspiration without losing the spot on the engaging surface 540.

In a released state shown in FIG. 17B, to disengage the "double pawl" 580 from the engaging surface 540, the user pushes the slider actuator 600 forward such that now it comes into contact with the second side 582 of the "double pawl" 580. The compression of the spring 610 causes the "double pawl" 580 to tilt backward and disengage from the engaging surface 540. In this position, a user can pull the plunger rod 520 in either direction for aspiration, filling, evacuating, or dosing an amount other than an amount specified by the interdental space or pitch of the plurality of spaced apart teeth 545.

Thus, aspects of the present dosing device provide a barrel having an open end and an opposing spaced apart port adapted to receive a needle; a plunger rod slidably disposed within said barrel through the barrel open end; the plunger rod having a plurality of spaced apart teeth over at least a portion of a top side thereof and having interdental spaces therebetween; a control component interconnecting said barrel and said plunger rod. In one embodiment, the control component comprises: a pawl comprising a first side having an end point engageable with the plurality of spaced apart teeth and a second end opposing the first side; means for causing the end point to enter an interdental space, engage a tooth and move the plunger rod forwardly an increment corresponding to the interdental space to allow for stepwise movement of the plunger rod within the barrel; an actuator for actuating the stepwise movement. In one embodiment, the actuator is movable from a resting position, wherein the end point engages a first tooth, to an actuated position, wherein the end point moves from the first tooth to a second tooth. In one embodiment, the control component further comprises a compressible slider actuator facing the second side of the pawl, the slider actuator is movable from a locked state to a released state, wherein in the locked state, the slider actuator is spaced apart from the second side of the pawl, and in the released state, the slider actuator impacts the second side of the pawl at an angle, and causes the end point of the first side to disengage from the plurality of spaced apart teeth. In one embodiment, in the released state, the plunger rod is freely slidable longitudinally the barrel.

In alternative embodiments, multiple engaging surfaces having variable teeth sizes can be used on different side of the plunger rod, such that different dose sizes can be dispensed with one single device by rotating, removing or replacing the plunger rod. The amount of dose variation is dependent on the pawl geometry, but is still driven by the interdental space or pitch of the rack(s).

Further embodiments consider the need, in some instances, to aspirate. This may be necessary in situations where the user wants to confirm that he/she is not injecting into a blood vessel (for instance, any sign of red within the syringe while aspirating is an indication that the needle is within a blood vessel). When the pawl is engaged, it typically sits somewhere between the rack teeth of the engaging surface. Therefore, it may allow for the rack to be pulled back slightly, before hitting a hard stop against the pawl (similar to backlash in gears). This feature can be utilized as an advantage since it allows for a consistent aspiration with each injection without impacting the ultimate dose that will be delivered (the user won't be able to skip teeth on the rack).

EXAMPLES

The present invention is especially useful with a cystoscope for injecting a pharmaceutical, such as botulinum toxin, into a target tissue, such as a bladder wall to treat a disease or condition such as a urological disease or condition (i.e. a bladder dysfunction such as overactive bladder), a prostate disorder, an ocular disease or condition or any other human ailment, condition or disease.

The normal micturition process is a result of a complex network of innervation of the bladder and urethral sphincter that ensures satisfactory bladder filling followed by timely voiding in healthy individuals. In order to achieve storage of urine in the bladder during the filling phase, the bladder neck and urethra remain closed and the detrusor muscle is relaxed (via stimulation of the noradrenalin beta receptors in the dome of the bladder). In the healthy bladder, when the pressure within the bladder is greater than that within the urethra, urination begins. The sensations of pain and bladder fullness are carried by the afferent fibers, which relay their message from the bladder to the micturition center in the pons of the brain triggering micturition. The voiding phase involves coordinated relaxation of the base of the bladder and urinary sphincter (via stimulation of the noradrenalin alpha receptors) and contraction of the detrusor muscle in the bladder wall secondary to inhibition of noradrenergic stimulation followed by parasympathetic stimulation via the neurotransmitter acetylcholine.

Overactive bladder is a condition resulting in a disruption to the normal micturition process. It is a syndrome complex characterized by urinary urgency, frequency and may or may not be accompanied by incontinence. Incontinence is due to involuntary contraction of the detrusor muscle during bladder filling (detrusor overactivity). Most cases of incontinence arise without obvious pathology. In such cases, abnormal detrusor contractions are termed idiopathic bladder overactivity. A smaller number of cases are secondary to neurogenic pathology and are termed neurogenic detrusor overactivity.

Neurogenic Detrusor Overactivity.

The pathophysiology of OAB is complex, involving peripheral and central nervous system (CNS) dynamics. Several CNS disorders are associated with the development of OAB, including spinal cord injury and multiple sclerosis. Neurological disease involving the spinal cord can result in incontinence secondary to a loss of inhibitory input from the micturition center and from interruption of the spinobulbospinal pathways which normally control bladder behavior. In the event of a spinal cord lesion, a change of balance of the effects of the afferent fibers, located between the muscle and submucosa of the bladder, is seen. The unmyelinated C fibers become functionally dominant and the detrusor hyperreflexia described in such patients is considered due to the reflex mediated by these unmyelinated C fibers.

The result, demonstrable on urodynamic evaluation, is abnormal involuntary detrusor contractions, often leading to incontinence. In addition, such patients frequently suffer from loss of coordinated relaxation of the urethral sphincters that normally precedes micturition. This lack of coordinated activity can result not only in incontinence but also in vesico-ureteric reflux which, if left untreated, can lead to potential renal damage.

Available Treatments.

Clean intermittent self-catheterization (CIC) is commonly used to drain the bladder, manage neurogenic incontinence and prevent vesico-ureteric reflux. When employing CIC, the patient inserts a catheter via the urethra into the bladder in order to void urine. CIC, however, can be associated with infection, which can exacerbate the problem of urinary incontinence and, in some circumstances, lead to renal damage. Common pharmacologic treatments to reduce bladder contractility include anticholinergics, antispasmodics and tricyclic antidepressants. However, these therapies are associated with a high incidence of side effects. Side effects of anticholinergics include dry mouth, constipation and blurred vision. Currently, the only options available to patients who do not respond to or discontinue anticholinergic therapy are invasive procedures such as implantable devices to chronically stimulate the sacral nerve or surgical bladder augmentation. While these procedures may be effective for some patients, they are highly invasive, do not necessarily guarantee continence, and may have long term complications.

BOTOX® (Botulinum Toxin Type A Purified Neurotoxin Complex) Treatment

Recently, studies have been carried out using BOTOX® (botulinum toxin) in the treatment of patients who suffer from bladder overactivity. Suppression of involuntary detrusor contractions has been attempted via the local administration of BOTOX® (botulinum toxin) to the detrusor muscle, which inhibits acetylcholine release by cleaving SNAP 25, a protein integral to successful docking and release of vesicles within the nerve endings, including acetylcholine, calcitonin gene-related peptides (CGRP), glutamate and substance-P. BOTOX® (botulinum toxin) is believed to inhibit the acetylcholine mediated detrusor contractions and may also inhibit other vesicle-bound neurotransmitters in both the afferent and efferent pathways of the bladder wall, urothelium or lamina propria.

There is evidence for the successful use of BOTOX® (botulinum toxin) in the management of neurogenic incontinence. It has been shown that botulinum toxin injections of 200 U to 300 U into the detrusor across 20 to 30 injection sites (10 units per mL per injection site) have been effective in restoring continence and enabling reduction or cessation of anticholinergic medication in such patients. In one study enrolling 21 patients, 17 of the 19 patients with follow-up data had restored continence within 6 weeks. To date, treatment of over 900 neurogenic overactive bladder patients with BOTOX® (botulinum toxin) at doses ranging from 200 U to 300 U in 20 to 30 injection sites has been reported. Treatment benefit has been described to last between 6 and 12 months with an acceptable side effect profile.

Endoscopy of the urinary bladder via the urethra is cystoscopy. Diagnostic cystoscopy is usually carried out with local anesthesia. General anesthesia is sometimes used for operative cystoscopic procedures.

When a patient has a urinary disease or condition, a physician can use a cystoscope 52, see FIG. 2 to see inside of the bladder and urethra. The urethra is the tube that carries urine from the bladder to the outside of the body. The cystoscope has lenses which permit the physician to focus on the inner surfaces of the urinary tract. Some cystoscopes use optical fibres (flexible glass fibres) that carry an image from the tip of the instrument to a viewing piece at the other end. The cystoscope is as thick as a pencil and has a light at the tip. Many cystoscopes have extra tubes to guide other instruments for surgical procedures to treat urinary problems.

There are two main types of cystoscopy—flexible and rigid—differing in the flexibility of the cystoscope. Flexible cystoscopy is carried out using local anesthesia on both sexes. Typically, lidocaine gel (such as the brand name Instillagel) is used as an anesthetic, instilled in the urethra. Rigid cystoscopy can be performed under the same conditions, but is generally carried out under general anesthesia, particularly in male subjects, due to the pain caused by the probe. The embodiments of our invention set forth herein (see eg the Figures) can be used to accurately and precisely inject a metered dose (aliquots) of a botulinum toxin (such as BOTOX®, DYSPORT®, MYOBLOC®, or XEOMIN®)

into the bladder wall (detrusor) of a patient to treat a bladder dysfunction. Our invention is not limited to use to treat a bladder dysfunction or to administration of a botulinum toxin, as it can be used for any therapeutic, cosmetic or research use in which accurate and precisely metered doses of an aqueous pharmaceutical is desired.

The present invention is useful for injecting a pharmaceutical, such as botulinum toxin, into a target tissue, such as a head and/or neck muscle to treat a disease or condition such as chronic migraine, or any other human ailment, condition or disease.

Studies have been carried out using BOTOX® (botulinum toxin) in the treatment of patients who suffer from chronic migraine. For example, it has been shown that botulinum toxin injections into certain head and neck muscles have been effective in treating chronic migraine. The recommended dilution is 200 Units/4 mL or 100 Units/2 mL, with a final concentration of 5 Units per 0.1 mL. The recommended dose for treating chronic migraine is 155 Units administered intramuscularly using a sterile 30-gauge, 0.5 inch needle as 0.1 mL (5 Units) injections per each site. Injections should be divided across 7 specific head/neck muscle areas as specified in the table below. A one inch needle may be needed in the neck region for patients with thick neck muscles. With the exception of the procerus muscle, which should be injected at one site (midline), all muscles should be injected bilaterally with half the number of injection sites administered to the left, and half to the right side of the head and neck. The recommended re-treatment schedule is every 12 weeks.

| Head/Neck Area | Recommended Dose (Number of Sites) |
| --- | --- |
| Frontalis | 20 Units divided in 4 sites (10 U each side) |
| Corrugator | 10 Units divided in 2 sites (5 U each side) |
| Procerus | 5 Units in 1 site |
| Occipitalis | 30 Units divided in 6 sites (15 U each side) |
| Temporalis | 40 Units divided in 8 sites (20 U each side) |
| Trapezius | 30 Units divided in 6 sites (15 U each side) |
| Cervical Paraspinal Muscle Group | 20 Units divided in 4 sites (10 U each side) |
| TOTAL DOSE: | 155 Units divided in 31 sites |

Each intramuscular injection site=0.1 mL=5 Units BOTOX®

The embodiments of our invention set forth herein can be used to accurately and precisely inject a metered dose (aliquots) of a botulinum toxin (such as BOTOX®) into certain head and/or neck muscles of a patient to treat chronic migraine. For example, each actuation of the dose injector can be measured to provide 0.1 ml (5 U) of BOTOX® for each intramuscular injection.

The present invention is not limited for use to treat chronic migraine or for administration of a botulinum toxin; as it can be used for any therapeutic, cosmetic or research use in which accurate and precisely metered doses of an aqueous pharmaceutical is desired. Accordingly, any and all modifications, variations or equivalent arrangements which may occur to those skilled in the art, should be considered to be within the scope of the present invention as defined in the appended claims.

Many alterations and modifications may be made by those having ordinary skill in the art without departing from the spirit and scope of the present disclosure. For example, features and aspects specifically discussed for one embodiment but not another may be interchangeable provided the modification does not conflict or made inoperable. Therefore, it must be understood that the illustrated embodiments have been set forth only for the purposes of examples, and that the embodiments should not be taken as limiting the disclosure as defined by the following claims. The following claims are, therefore, to be read to include not only the combination of elements which are literally set forth, but all equivalent elements for performing substantially the same function in substantially the same way to obtain substantially the same result. The claims are thus to be understood to include those that have been illustrated and described above, those that are conceptually equivalent, and those that incorporate the ideas of the present disclosure.

What is claimed is:

1. A dosing device comprising:
a barrel having an open end and an opposing spaced apart port adapted to receive a needle; a plunger rod slidably disposed within said barrel through the barrel open end; the plunger rod having a plurality of spaced apart teeth over at least a portion of a top side thereof and having interdental spaces therebetween;
a control component interconnecting said barrel and said plunger rod; the control component comprising:
a pawl comprising a first side having an end point engageable with the plurality of spaced apart teeth and a second side opposing the first side; means for causing the end point to enter an interdental space, engage a tooth and move the plunger rod forwardly an increment corresponding to the interdental space to allow for stepwise movement of the plunger rod within the barrel; an actuator for actuating the stepwise movement; wherein the actuator is movable along a vertical axis perpendicular to the plunger rod from a resting position, wherein the end point engages a first tooth, to an actuated position, wherein the end point moves from the first tooth to a second tooth; and
a compressible slider actuator facing the second side of the pawl, and movable from a locked state to a released state, wherein in the locked state, the slider actuator is spaced apart from the second side of the pawl, and in the released state, the slider actuator impacts the second side at an angle, and causes the end point of the first side to disengage from the plurality of spaced apart teeth;
and wherein in the released state, the plunger rod is freely slidable longitudinally the barrel.

* * * * *